US006794361B1

(12) United States Patent
Lewis et al.

(10) Patent No.: US 6,794,361 B1
(45) Date of Patent: Sep. 21, 2004

(54) PEPTIDES

(75) Inventors: Richard James Lewis, Woolloongabba (AU); Paul Francis Alewood, Moggill (AU); Iain Andrew Sharpe, Taringa (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/787,986

(22) PCT Filed: Oct. 1, 1999

(86) PCT No.: PCT/AU99/00844

§ 371 (c)(1),
(2), (4) Date: Jun. 27, 2001

(87) PCT Pub. No.: WO00/20444

PCT Pub. Date: Apr. 13, 2000

(30) Foreign Application Priority Data

Oct. 2, 1998 (AU) .............................................. PP6274

(51) Int. Cl.$^7$ ............................ C07K 7/00; C07K 7/64; A61K 38/04
(52) U.S. Cl. ................................ 514/9; 514/2; 514/14; 530/300; 530/327; 530/344; 530/345; 435/69.7; 435/320.1; 435/252.3; 536/23.4; 536/23.5
(58) Field of Search .................... 514/2, 9, 14; 530/300, 530/327, 344, 345; 435/69.7, 320.1, 252.3; 536/23.4, 23.5

(56) References Cited

U.S. PATENT DOCUMENTS 5,441,985 A    8/1995  Foreman ..................... 514/646

FOREIGN PATENT DOCUMENTS

| WO | WO 91/07980 | 6/1991 |
| WO | WO 96/14079 | 5/1996 |
| WO | WO 96/40064 | 12/1996 |
| WO | WO 97/01351 | 1/1997 |
| WO | WO 97/30997 | 8/1997 |
| WO | WO 98/02148 | 1/1998 |
| WO | WO 98/05309 | 2/1998 |
| WO | WO 98/22126 | 5/1998 |
| WO | WO 98/51668 | 11/1998 |
| WO | WO 00/44769 | 8/2000 |

OTHER PUBLICATIONS

Sawynok, J. et al., "Peripheral antinociceptive actions of desipramine and fluoxetine in an inflammatory and neuropathic pain test in the rat", Pain 82(2): 149–158 (Aug. 1999).
Ardid, D. et al., "Comparative effects of different uptake inhibitor antidepressants in two pain test in mice", Fundam, Clin., Pharmacology 6(2): 75–82, 1992.
Kawamata, et al., "Analgesic effect of intrathecal desipramine on carrageenan–induced thermal hyperalgesia in the rat", Br. J. Anaesth 83(3): 449–452 (Sep. 1999).

Reimann, et al., "The Antinociceptive Effects of Morphine, Desipramine, and Sertonin and Their Combinations After Intrathecal Injection in the Rat", Anesth Analg 88(1): 141–145 (Jan. 1999).
Bowersox, S. S. et al., "Selective N–Type Neuronal Voltage–Sensitive Calcium Channel Blocker, SNX–111, Produces Spinal Antinociception in Rat Models of Acute, Persistent and Neuropathic Pain", The Journal of Pharmacology& Experimental Therapeutics 279(3):1243–1249 (1996).
Krames, E. S. et al., "Intrathecal D–Ala2–D–Leu5–enkephalin (DADL) Restores Analgesia in a Patient Analgetically Tolerant in Intrathecal Morphine Sulfate", Pain 24:205–209 (1986).
Takagi, H. et al., "Analgesic effect of L–threo–3,4–dihydroxyphenylserine (L–DOPS) in patients with chronic pain", Eur pean Neurophychopharmacology 6:43–47 (1996).
Eisenach, J. C. et al., "Intrathecal, but Not Intravenous, Clonidine Reduces Experimental Thermal or Capsaicin–Induced Pain and Hyperalgesia in Normal Volunteers", Anesth Analg 87(3):591–596 (1998).
Dubner, R. et al., "The Neurobiology of Pain and Its Modulation", The Clinical Journal of Pain 5(Suppl. 2):S1–S6 (1989).
Dyck, P. J. et al., "New Understanding and Treatment of Diabetic Neuropathy", The New England Journal of Medicine 326(19):1287–1288 (1992).
Atkinson, J. H. et al., "A placebo–controlled randomized zlinical trial of nortriptyline for chronic low back pain", Pain 76:287–296 (1998).
Mico, J. A. et al., "Implication of B1– and B2–adrenergic receptors in the antinociceptive effect of tricyclic antidepressants", European Neuropsychopharmacology 7:139–145 (1997).
Springer, J. P. et al., "Facilitory and Inhibitory Effects of Selective Norepinephrine Reuptake Inhibitors on Hypogastric Nerve–Evoked Urethral Contractions in the Cat: A Prominent Role of Urethral B–Adrenergic Receptors", The Journal of Urology 152:515–519 (1994).
Dinan, T. G. et al., "Assessment of Central Noradrenergic Functioning in Irritable Bowel Syndrome Using a Neuroendocrine Challenge Test", Journal of Psychosomatic Research 34(5):575–580 (1990).

(List continued on next page.)

Primary Examiner—Christopher S. F. Low
Assistant Examiner—Chih-Min Kam
(74) Attorney, Agent, or Firm—Scully, Scott, Murphy & Presser

(57) ABSTRACT

The invention relates to an isolated, synthetic or recombinant χ-conotoxin peptide having the ability to inhibit a neuronal amine transporter, nucleic acid molecules encoding all or part of such peptides, antibodies to such peptides and uses and methods of tre

OTHER PUBLICATIONS

Figure 1:
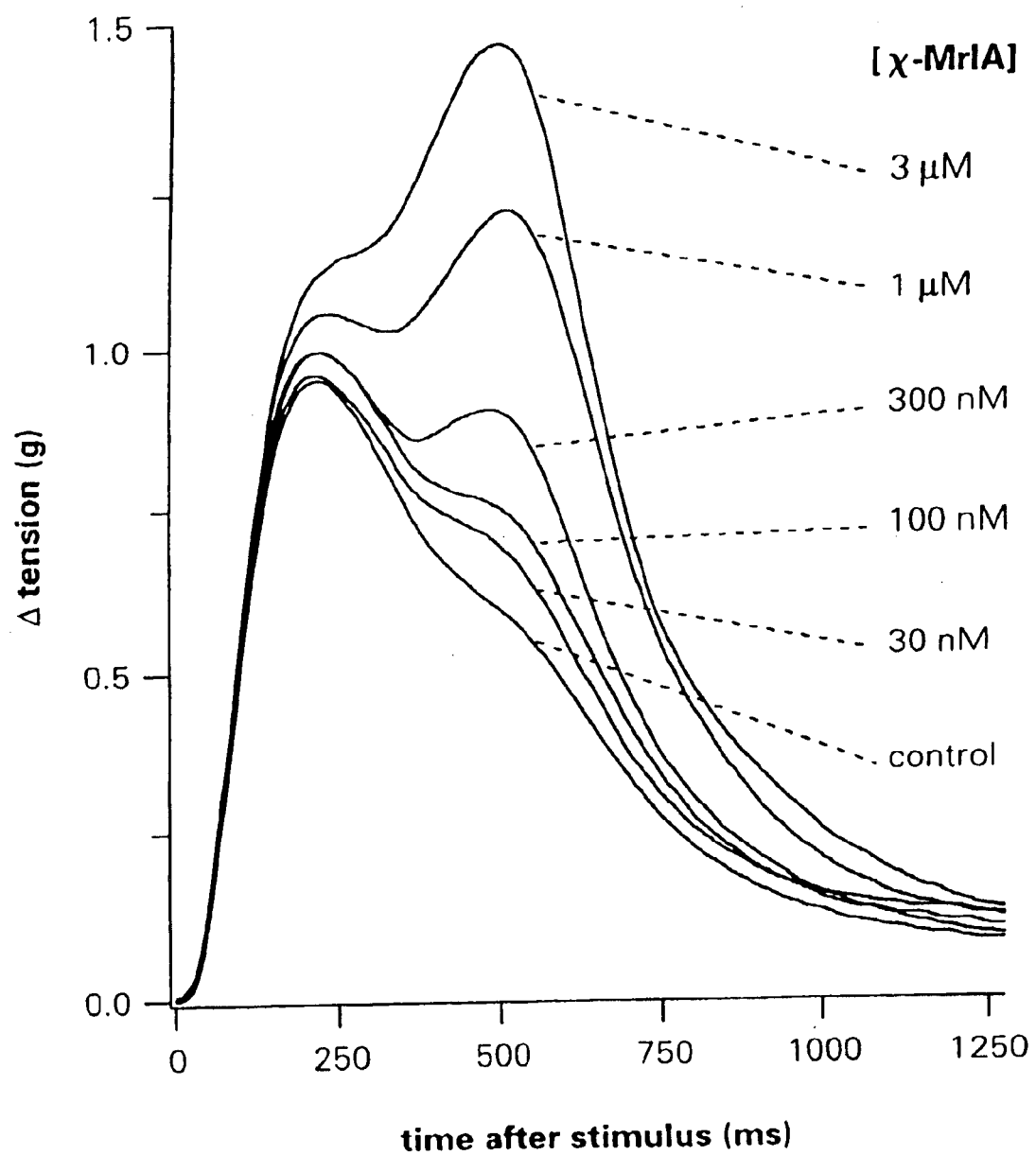

Leung, D. et al., "Protease Inhibitors: Current Status and Future Prospects", *Journal of Medicinal Chemistry* 43(3):305–341 (2000).

O'Neill, M. J et al., "Effects of Ca2+ and Na+ channel inhibitors in vitro and in global cerebal ischaemia in vivo", *European Journal of Pharmacology* 332:121–131 (1997).

Eisenach, J. C. et al., "Cerebrospinal Fluid Norepinephrine and Acetylcholine Concentrations During Acute Pain", *Anesth Analg* 82(3):621–626 (1996).

Marban, E. et al., "Structure and function of voltage–gated soidum channels", *Journal of Physiology* 508(3):647–657 (1998).

Yanagawa, Y. et al., "A Novel Sodium Channel Inhibitor from *Conus geographus*: Purification, Structure, and Pharmacological Properties", *Biochemistry* 27:6256–6262 (1988).

Ryan, J. et al., "Evaluation of an enkephalin analog in men with castor oil–induced diarrhea", *Clin Pharmacol Ther* 39:40–42 (1986).

Penttila, O. et al., "Studies of Rectal Mucosal Catecholamines in Ulcerative Colitis", *Annals of Clinical Research* 7:32–36 (1975).

Yaksh, T.L., "Pharmacology of Spinal Adrenergic Systems Which Modulate Spinal Nociceptive Processing", *Pharmacology Biochemistry & Behavior* 22: 845–858 (1985).

Yaksh T.L. & Takano, Y. "Characterization of the Pharmacology of Intrathecally Administered Alpha–2 Agonists and Antagonists in Rats", *J. Pharmacology & Experimental Therapeutics* 261 (2): 764–772 (1992).

Yaksh, T.L. & Howe, J.R., "Changes in Sensitivity to Intrathecal Norepinephrine and Serotonin after 6–Hydroxydopamine (6–OHDA), 5,6–Dihydroxytryptamine (5,6–DHT) or Repeated Monoamine Administration", *J. Pharmacology & Experimental Therapeutics* 220(2): 311–321 (1982).

Howe, J.R., et al., "Selective Antagonism of the Antinociceptive Effect of Intrathecally Applied Alpha Adrenergic Agonists by Intrathecal Prazosin and Intrathecal Yohimbine", *J. Pharmacology & Experimental Therapeutics* 224(3): 552–558 (1983).

Solomon, et al., "Pharmacological Characterization of Alpha Adrenoceptors Involved in the Antinociceptive and Cardiovascular Effects of Intrathecally Administered Clonidine",*J. Pharmacology & Experimental Therapeutics* 251(1): 28–38 (1989).

Fleetwood–Walker, S.M. et al., "An $a_2$ Receptor Mediates the Selective Inhibition by Noradrenaline Responses of Identified Dorsal Horn Neurones", *Brain Research*, 334: 243–254 (1985).

PEPTIDES

This application is a 371 of PCT/AU99/00844, filed Oct. 1, 1999, which claims priority to Australia Patent Application Serial No. PP 6274, filed Oct. 1, 1998.

The present invention relates to novel peptides and derivatives thereof useful as inhibitors of neuronal amine transporters of neurotransmitters such as noradrenaline, serotonin, dopamine, glutamic acid and glycine. The invention also relates to pharmaceutical compositions comprising these peptides, nucleic acid probes useful in finding active analogues of these peptides, assays for finding compounds having neuronal noradrenaline transporter inhibitory activity and the use of these peptides in the prophylaxis or treatment of conditions such as but not limited to incontinence, cardiovascular conditions and mood disorders.

The marine snails of the genus Conus (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of receptors and ion-channels. The venom from any single Conus species may contain more than 100 different peptides. The conotoxins are divided into classes on the basis of their physiological targets. To date, ten classes have been described. The ω-conotoxin class of peptides target and block voltage-sensitive $Ca^{2+}$-channels inhibiting neurotransmitter release. The α-conotoxins and ψ-conotoxins target and block nicotinic ACh receptors, causing ganglionic and neuromuscular blockade. Peptides of the µ-conotoxin class act to block voltage-sensitive $Na^+$-channels inhibiting muscle and nerve action potentials. The δ-conotoxins target and delay the inactivation of voltage-sensitive $Na^+$-channels, enhancing neuronal excitability. The κ-conotoxin class of peptides target and block voltage-sensitive $K^+$-channels, and these also cause enhanced neuronal excitability. The conopressins are vasopressin receptor antagonists and the conantokins are NMDA receptor antagonists. More recently, the prototype of a new γ-conotoxin class, which targets a voltage-sensitive nonspecific cation channel, and of a new σ-conotoxin class, which antagonises the $5HT_3$ receptor, have been described.

It has now been found that a new class of conotoxin exists, hereinafter referred to as the χ-conotoxin class, which are characterised by having the ability to inhibit neuronal amine transporters.

Compounds which inhibit neurotransmitter reuptake have been found to be useful in the treatment of lower urinary tract disorders, such as urinary incontinence, detrusor instability and interstitial cystitis. One such compound is "imipramine" which, in addition to inhibiting noradrenaline reuptake, has been shown to affect calcium channel blockade, and to exhibit anticholinergic, local anaesthetic activity and a number of other effects. Other compounds capable of inhibiting noradrenaline reuptake are described in U.S. Pat. No. 5,441,985. These compounds are said to have a reduced anticholinergic effect relative to imipramine.

In the case of the peptides of the present invention this inhibition of neurotransmitter reuptake is achieved by selectively inhibiting the neuronal neurotransmitter transporter, such as the noradrenaline transporter, which functions to rapidly clear released noradrenaline from the synapse back into neurons.

The peptides of the present invention are the first peptides to have activity in inhibiting an amine transporter. All other conotoxin peptides characterised to date target ion channels or receptors on cell surfaces.

According to one aspect of the present invention there is provided an isolated, synthetic or recombinant χ-conotoxin peptide having the ability to inhibit a neuronal amine transporter.

Preferably, the neuronal amine transporter is the neuronal noradrenaline transporter.

The χ-conotoxin peptide may be a naturally occurring peptide isolated from a cone snail, or a derivative thereof.

Preferably the χ-conotoxin peptide is χ-MrIA or χ-MrIB, or a derivative thereof. χ-MrIA and χ-MrIB may be isolated from the venom of the mollusc hunting cone snail, *Conus marmoreus*.

They are both peptides of 13 amino acid residues in length, and contain 2-disulphide bonds; the peptides show most homology to members in the α-conotoxin class, which act as nicotinic ACh receptor antagonists.

The amino acid sequences of χ-MrIA and χ-MrIB are as follows:

χ-MrIA NGVCCGYKLCHOC SEQ ID NO. 1
χ-MrIB VGVCCGYKLCHOC SEQ ID NO. 2

The C-terminus may be a free acid or amidated.

In the sequences above the "O" refers to 4-hydroxy proline (Hyp). This amino acid residue results from post translational modification of the encoded peptide and is not directly encoded by the nucleotide sequence.

Preferably, the χ-conotoxin peptide is a selective inhibitor of the neuronal noradrenaline transporter. The terms "selective" and "selectively" as used herein mean that the activity of the peptide as an inhibitor of neuronal noradrenaline transporter is considerably greater than any activity at the $α_1$-adrenoceptors.

U.S. Pat. No. 5,441,985 indicates that inhibitors of noradrenaline reuptake which have a negligible anticholinergic effect are particularly useful in the treatment of lower urinary tract disorders. It has been found that χ-MrIA also has no detectable anticholinergic effect.

Accordingly in a preferred embodiment of the invention there is provided an isolated, synthetic or recombinant χ-conotoxin peptide having the ability to selectively inhibit neuronal noradrenaline transporter, and having negligible or no anticholinergic effect.

χ-MrIA has also been found to have no activity as a sodium channel blocker or as an inhibitor of dopamine transporter. The absence in χ-MrIA of these additional pharmacological activities commonly associated with other noradrenaline transporter inhibitors and in preferred peptides according to the invention, makes these peptides useful pharmacological tools.

The χ-conotoxin peptides according to the invention may be naturally occurring peptides, such as χ-MrIA and χ-MrIB, or may be derivatives of naturally occurring peptides.

The term "derivative" as used herein in connection with naturally occurring χ-conotoxin peptides, such as χ-MrIA and χ-MrIB, refers to a peptide which differs from the naturally occurring peptides by one or more amino acid deletions, additions, substitutions, or side-chain modifications. Such derivatives which do not have the ability to inhibit neuronal noradrenaline transporter do not fall within the scope of the present invention.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size, for example
Ser⇌Thr⇌Pro⇌Hyp⇌Gly⇌Ala, Val⇌Ile⇌Leu,
His⇌Lys⇌Arg, Asn⇌Gln⇌Asp⇌Glu or Phe⇌Trp⇌Tyr.
It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a peptide is substituted with an amino acid having different properties, such as naturally-occurring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

Additions encompass the addition of one or more naturally occurring or non-conventional amino acid residues. Deletion encompasses the deletion of one or more amino acid residues.

As stated above the present invention includes peptides in which one or more of the amino acids has undergone sidechain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residue may be modified by, for example, hydroxylation in the 4-position.

A list of some amino acids having modified side chains and other unnatural amino acids is shown in Table 1.

TABLE 1

| Non-conventional amino acid | Code |
| --- | --- |
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |

TABLE 1-continued

| Non-conventional amino acid | Code |
|---|---|
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethylglycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethylglycine | Nnbhe |
| O-methyl-L-serine | Omser |
| O-methyl-L-homoserine | Omhser |

These types of modifications may be important to stabilise the peptide if administered to an individual or used as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

The χ-conotoxins of the present invention are typically amidated at the C-terminal, however compounds with a free carboxyl terminus or other modifications at the C-terminal are considered to be within the scope of the present invention. Preferably the peptides are amidated or have a free carboxyl at the C-terminal.

Preferably the derivatives of naturally occurring χ-conotoxin peptides will retain the Cys residues and characteristic disulphide bonding pattern. Derivatives may include additional Cys residues provided they are protected during formation of the disulphide bonds.

In modification to form derivatives of naturally occurring χ-conotoxin peptides it is useful to compare the amino acid sequences of active naturally occurring peptides to determine which, if any, of the residues are conserved between active species. Substitution of these conserved residues, while not prohibited, is less favoured than substitutions of nonconserved residues.

Derivatives where Ala replaces one or more residues can be used to identify the pharmacophore. Preferably only one or two amino acids is replaced with Ala at a time. Additional new peptides can be made where charged, polar or hydrophobic residues, respectively, are replaced to assist defining more precisely the type of interactions involved in the binding of this pharmacological class of peptide to its receptor. Non-conservative replacements, where charge is reversed, or polar residues replace hydrophobic residues, can further identify residues involved in binding. All of these peptides have potential to show improved potency, or greater selectivity. Non-native amino acid changes could also be included to improve potency, selectivity and/or stability.

Exposed residues are most likely to be involved in receptor binding and can be systematically replaced. Particular emphasis is placed on changing residues involved in binding and residues just on the periphery of the pharmacophore, using longer side chain forms or non-conserved changes to pick up additional binding interactions for improved potency and/or selectivity. Reducing or enlarging loop sizes and the tail of MrIA or MrIB further modifies activity.

It is noted that MrIA and MrIB are composed of a tail (residues 1–3), and two loops (residues 6–9 and 11–12), however the χ-conotoxin peptides and derivatives of the present invention are not restricted to those having this particular arrangement of amino acids and disulphide bonds. Other arrangements are also possible, and provided the resultant peptide has the requisite activity, a peptide will fall within the scope of the present invention. Preferably the peptides will have at least two cysteine residues and at least one disulphide bond, or more preferably four cysteine residues and two disulphide bonds.

The connectivity of the disulfide bonds in these peptides may be A-B/C-D, A-C/B-D or A-D/B-C, the latter being preferred for MrIA and MrIB. A, B, C and D refer to the first, second, third and fourth Cys residues involved in disulphide bond formation, respectively.

These peptides can also be labelled and used to establish binding assays to identify new molecules that act at the same site. For example, labelled ligand of MrIA or MrIB could have tritium included or may have radio-active iodine or similar attached through a Tyr or other appropriate residue. A Tyr scan through each peptide will establish a suitable location for incorporation of the Tyr. The inhibition of binding of such labelled peptides to tissue homogenates or expressed transporters by compounds or mixtures would permit identification of new peptides active at this site, including peptides present in serum and nerve and muscle tissue of mammals, including human tissues. The assay will also allow identification of non-peptide molecules that also act at the same site as MrIA and MrIB, and that may have utility as orally active forms of these peptides. Labelled peptides will additionally permit autoradiographic studies to identify the location of the peptide binding across various tissues.

Portions of these sequences can be used to search ESTR data bases to identify in mammals peptides or proteins that contain related sequence information that could be used to identify endogenous ligands that act in a similar manner in mammals.

The χ-conotoxins of the present invention may be prepared using standard peptide synthetic methods followed by oxidative disulfide bond formation. For example, the linear peptides may be synthesised by solid phase methodology using BOC chemistry, as described by Schnoltzer et al (1992). Following deprotection and cleavage from the solid support the reduced peptides are purified using preparative chromatography. The purified reduced peptides are oxidised in buffered systems, for example as described in example 2. The oxidised peptides were purified using preparative chromatography.

References describing the synthesis of conotoxins include Sato et al, Lew et al and WO 91/07980.

The χ-conotoxins may also be prepared using recombinant DNA technology. A nucleotide sequence encoding the desired peptide sequence may be inserted into a suitable vector and protein expressed in an appropriate expression system. In some instances, further chemical modification of the expressed peptide may be appropriate, for example C-terminal amidation. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

The invention further provides an isolated nucleic acid molecule comprising a sequence of nucleotides encoding or complementary to sequence encoding a χ-conotoxin peptide as described above.

In a further aspect of the present invention there is provided a nucleic acid probe comprising a sequence of nucleotides encoding or complementary to a sequence encoding all or part of a χ-conotoxin peptide.

In a particularly preferred embodiment the nucleic acid probe comprises a sequence of nucleotides encoding or complementary to a sequence encoding the sequence shown in SEQ ID NO: 1 or SEQ ID NO: 2.

As used herein a reference to a "probe" includes reference to a primer used in amplification or a probe for use in direct hybridization.

Still another aspect of the present invention is directed to antibodies to the χ-conotoxin peptides according to the invention. Such antibodies may be monoclonal or polyclonal and may be selected from naturally occurring antibodies to the peptides or may be specifically raised to the peptides using standard techniques. In the case of the latter, the peptides may first need to be associated with a carrier molecule. The antibodies of the present invention are particularly useful as therapeutic or diagnostic agents.

In this regard, specific antibodies can be used to screen for the peptides according to the invention. Techniques for such assays are well known in the art and include, for example, sandwich assays and ELISA. Knowledge of peptide levels may be important for monitoring certain therapeutic protocols.

It may also be possible to prepare antiidiotypic antibodies using techniques known to the art. These antiidiotypic antibodies and their use as therapeutic agents represent a further aspect of the present invention.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli*, Bacillus sp and Pseudomonas sp. Preferred eukaryotic cells include yeast, fungal, mammalian and insect cells.

Accordingly, another aspect of the present invention contemplates a genetic construct comprising a vector portion and a gene capable of encoding a peptide according to the invention.

Preferably, the gene portion of the genetic construct is operably linked to a promoter on the vector such that said promoter is capable of directing expression of the gene portion in an appropriate cell.

The present invention extends to such genetic constructs and to prokaryotic or eukaryotic cells comprising same.

Chimeras of χ-conotoxins such as MrIA, with other conotoxins or additionally with other peptides or proteins, can be made to engineer the activity into other molecules, in some instances to produce a new molecule with extra functionality. This would preferably be done using the segment or segments of the sequence of these peptides that contain the pharmacophore. Where the pharmacophore is discontinuous, the segments making up the pharmacophore should be positioned in the new construct to allow binding to the receptor. Chimeras with other conotoxins may include additional Cys residues and additional disulphide bonds.

It is common for conotoxin peptides within an activity class to have a similar pattern of disulphide bonding, with peptide loops between the respective cysteine residues. For χ-MrIA and χ-MrIB disulphide bonds link the first and fourth, and the second and third cysteine residues. This pattern is different from the binding pattern observed for α-conotoxin peptides. Despite this difference chimeric derivatives may be prepared by substituting a loop of a χ-conotoxin peptide with the loop comprising a sequence from another peptide, including α-conotoxin.

The invention also includes dimers, trimers, etc. of χ-conotoxin peptides as well as χ-conotoxin peptides bound to other peptides.

Preferably the χ-conotoxin peptides according to the invention have 10 to 30 amino acids, more preferably 11 to 20.

The complete gene sequence for the naturally occurring χ-conotoxin peptides may be obtained using a combined 5' RACE and 3' RACE strategy coupled with cloning and DNA sequencing.

The χ-conotoxin peptides according to the present invention are active in inhibiting neuronal noradrenaline transporter. Accordingly the invention provides the use of a χ-conotoxin peptide as an inhibitor of neuronal noradrenaline transporter, and in the treatment or prophylaxis of diseases or conditions in relation to which the inhibition of neuronal noradrenaline transporter is associated with effective treatment. Such activity in pharmacological agents is associated with activity in the prophylaxis or treatment of diseases or conditions of the urinary or cardiovascular systems, or mood disorders, or in the treatment or control of pain or inflammation.

Accordingly the present invention provides a method for the treatment or prophylaxis of urinary or cardiovascular conditions or diseases or mood disorders or for the treatment or control of pain or inflammation including the step of administering to a mammal an effective amount of an isolated, synthetic or recombinant χ-conotoxin peptide having the ability to inhibit neuronal noradrenaline transporter.

Examples of diseases or conditions of the urinary system include urinary and fecal incontinence. Examples of cardiovascular diseases or conditions include arrhythmias of various origins and coronary heart failure. Examples of mood disorders include depression, anxiety and cravings, such as smoking. Examples of pain include chronic pain, neuropathic pain and inflammatory pain.

Preferably the mammal is in need of such treatment although the peptide may be administered in a prophylactic sense.

The invention also provides a composition comprising an isolated, synthetic or recombinant χ-conotoxin peptide having the ability to inhibit neuronal noradrenaline transporter, and a pharmaceutically acceptable carrier or diluent.

Preferably the composition is in the form of a pharmaceutical composition.

There is also provided the use of an isolated, synthetic or recombinant χ-conotoxin peptide having the ability to inhibit neuronal noradrenaline transporter in the manufacture of a medicament for the treatment or prophylaxis of urinary or cardiovascular conditions or diseases, or mood disorders, of for the treatment or control of pain or inflammation.

It is also noted that noradrenaline transporter is expressed not only by nerve cells, but also by other tissues including the placenta, pulmonary endothelial cells and the uterus. The peptides according to the present invention may also be effective in inhibiting these noradrenaline transporters, and may be useful in treating conditions in which these transporters are implicated.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

The pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

Those skilled in the art may readily determine appropriate formulations for the peptides or modified peptides of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various of the other ingredients such as these enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying a of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions and gels, or compositions suitable for inhalation or intranasal delivery, for example solutions or dry powders.

Parenteral dosage forms are preferred, including those suitable for intravenous, intrathecal, intracerebral or epidural delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 $\mu$g to about 2000 mg. Expressed in proportions, the active compound is generally present in from about 0.25 $\mu$g to about 200 mg/ml of carrier. In the case of compositions containing supplementary active ingredients, the dosages are determined by reference to the usual dose and manner of administration of the said ingredients.

The invention will now be described with reference to the accompanying drawings and examples, however it is to be understood that the particularity of the following description is not to supersede the generality of the preceding description of the invention.

Referring to the figures:

FIG. 1 is a graphical representation showing the typical effect of $\chi$-MrIA on the time course of the contraction of the bisected rat prostatic vas deferens to field stimulation with a single supramaximal pulse (55 V, 1 ms). $\chi$-MrIA (30 nM–3 $\mu$M) was added to the organ bath cumulatively in half log unit steps.

Figure 2:
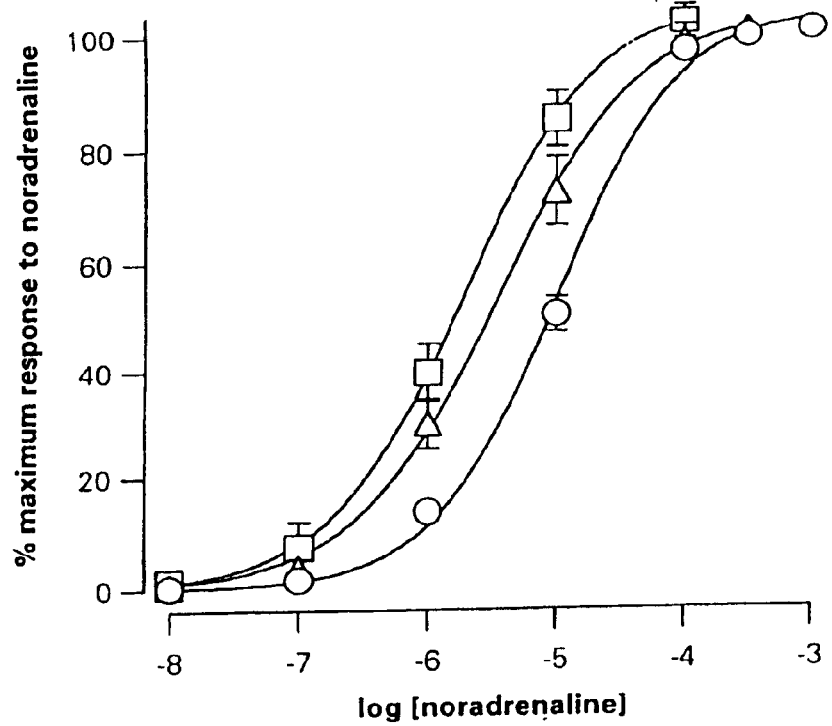
Figure 2:
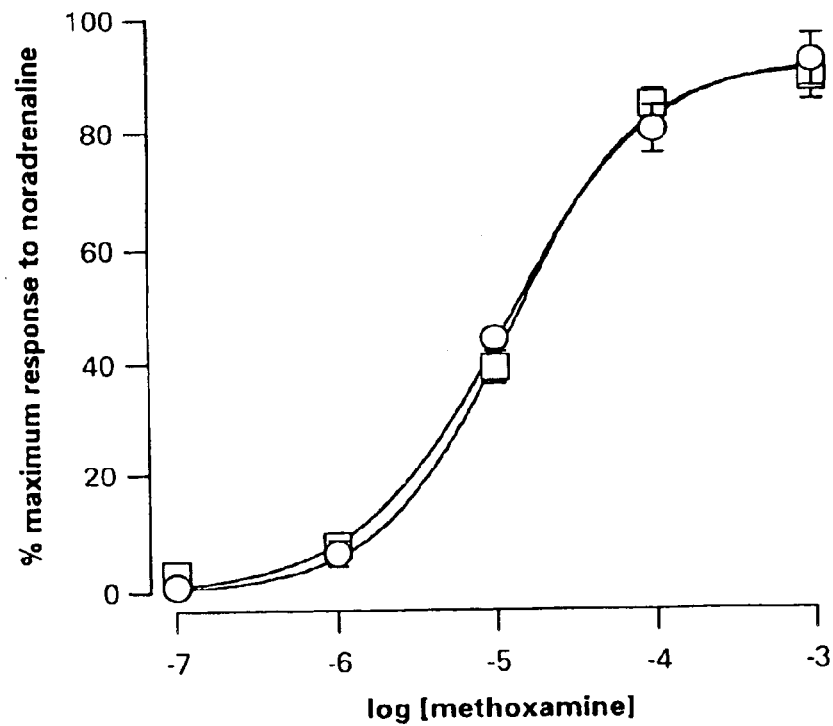

FIG. 2 is a graphical representation of the effect of $\chi$-MrIA, -MrIA on contractile responses of bisected portions of the rat epididymal vas deferens to exogenous $\alpha_1$-adrenoceptor agonists. (a) log concentration-response curves to noradrenaline in the absence (○) and the presence of 1 $\mu$M ($\Delta$) or 3 $\mu$M ($\square$) in $\chi$-MrIA, -MrIA. (b) log concentration-response curves to methoxamine in the absence (○) and the presence ($\square$) of 3 $\mu$M $\chi$-MrIA. Each data point in (a) and (b) represents the mean ±SEM of observations from 4–5 individual tissue preparations. Some error bars are obscured by the symbols.

Figure 3:
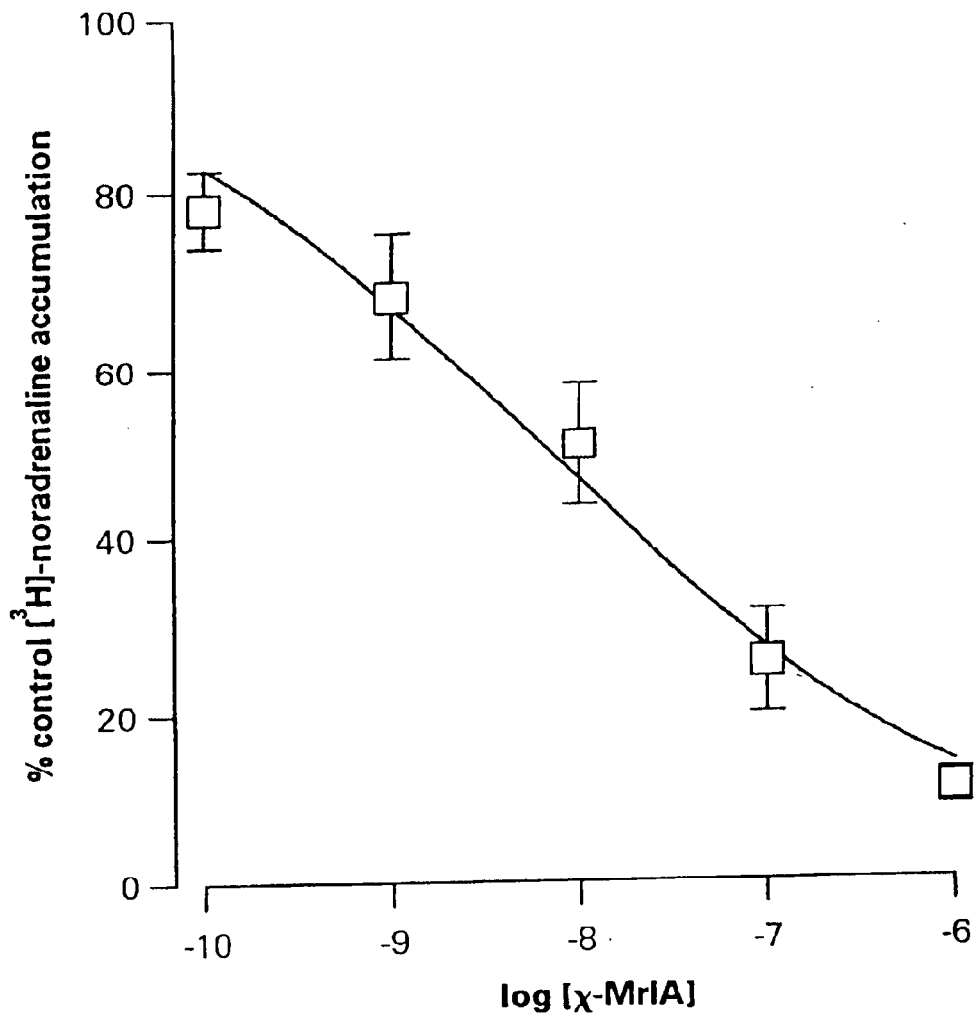

FIG. 3 is a graphical representation showing inhibition by $\chi$-MrIA on the desipramine sensitive accumulation of [$^3$H]-noradrenaline by Chinese Hamster Ovary (CHO) cells transfected with the cDNA clone for the human neuronal noradrenaline transporter. Accumulation of [$^3$H]-noradrenaline is expression as a percentage of the cellular uptake in the absence of $\chi$-MrIA. Data points represent the mean ±SEM or observations from 4 separate experiments.

Figure 4:
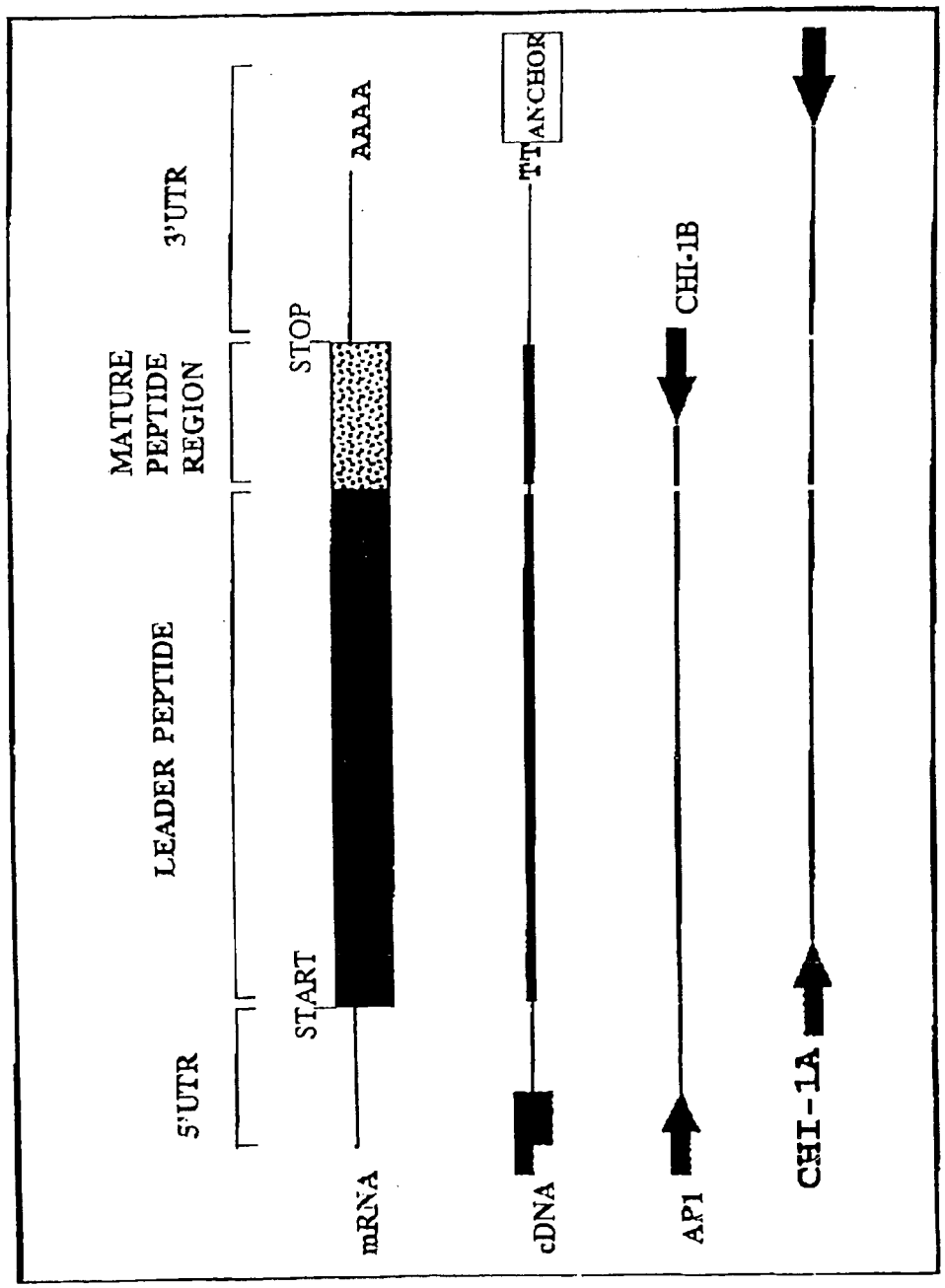

FIG. 4 is a diagrammatic representation showing derivation of coneshell venom peptide sequences. 5'RACE PCR using the primers AP1+CHI-1B produce the 5' UTR and leader peptide sequence which is then used to generate the PCR primers specific for $\chi$-conotoxins. The 3' UTR using the primers CHI-1A+ANCHOR completed the derivation of the remaining mature peptide sequence and 3' UTR sequence.

EXAMPLES

Drugs

The drugs used in this and the following examples include: desiprarine hydrochloride (Sigma); indomethacin (Sigma); methoxamine hydrochloride (Sigma); (−)-noradrenaline bitartrate (Sigma); [$^3$H]-1-noradrenaline (specific activity 2200 Ci/mM; New England Nuclear, Boston, Mass., U.S.A.); tetrodotoxin (Sigma); yohimbine hydrochloride (Sigma).

Statistical Analysis

Data for the examples below are expressed as the mean and standard error of 4–6 experiments. Sigmoidal curve-fitting for the calculation of $EC_{50}$ values was performed by non-linear regression using the software package Igor Pro (WaveMetrics). Differences between means were assessed by Student's t test (two-tailed) using the software package Prism (GraphPad). Values of $P<0.05$ were taken to indicate statistically significant differences.

Example 1

Rat Vas Deferens Preparation

Male Wistar rats (250–350 g) were killed by a blow to the head and the vasa deferentia were removed. Each tissue was divided into bisected epididymal and prostatic portions. The tissue segments were mounted in 5 mL organ baths under a tension of 0.5 g. The bathing solution had the following composition (mM): NaCl, 119; KCl, 4.7; $MgSO_4$, 1.17; $KH_2PO_4$, 1.18; $NaHCO_3$, 25.0; glucose, 5.5; $CaCl_2$, 2.5; EDTA, 0.026; was maintained at 37° C. and bubbled with 5% v/v $CO_2$ in $O_2$. The preparations were equilibrated for at least 45 min prior to the commencement of experimentation. Contractions were registered by means of an isometric force transducer (Narco Bio-System F-60) and were recorded on a Power Macintosh computer using Chart version 3.5.4/s software and a MacLab/8s data acquisition system (ADInstruments) at a sampling frequency of 200 Hz.

The bisected prostatic segments were used to examine the effect of $\chi$-MrIA on the electrically evoked contraction of the smooth muscle mediated by sympathetic neurotransmission. The tissue preparations were straddled with platinum stimulating electrodes. Electrical field stimulation (EFS) was made at 3 min intervals using a single 55 V pulse of 1 ms duration generated by a Grass S44 Stimulator. The contractions could be blocked by tetrodotoxin (0.1 $\mu$M), indicating they were neurally mediated. Increasing concentrations of the peptide were added to the organ bath cumulatively in half log unit increments. Each dose was applied once the effect of the previous dose on the response to electrical stimulation had attained a steady level.

Effect of $\chi$-MrIA on Sympathetic Neurotransmission

The bisected portions of the prostatic rat vas deferens responded to field stimulation with a biphasic contraction. In this preparation, the two components of the biphasic contraction were well separated temporally. The first part of the response was the dominant one, and reached a maximum level approximately 200 ms after delivery of the electrical pulse. The second phase of the contraction peaked approximately 500 ms after stimulation. Our attempts to identify the pharmacological activity of $\chi$-MrIA began with an investigation of its effects in the field stimulated rat vas deferens. The effect of $\chi$-MrIA on the response of the preparation to field stimulation is shown in FIG. 1. The conotoxin (30 nM–3 $\mu$M) acted to increase the second phase of the contraction. This effect was found to be concentration dependent. By subtracting the control response from traces obtained in the presence of $\chi$-MrIA, the specific enhancement by the peptide of only the second component of the contraction becomes apparent. A concentration-response curve for $\chi$-MrIA acting to specifically potentiate the second component can also be constructed.

The action of $\chi$-MrIA on the electrically evoked response was highly specific, enhancing only the second component of the biphasic response. This late phase of the contraction is recognised to be mediated by noradrenaline, and is selectively inhibited by prazosin and other $\alpha_1$-adrenoceptor antagonists. The first phase of the contraction, which is due to the activation of postjunctional $P_{2x}$-purinoceptors by released ATP, was not similarly enhanced. The magnitude of the noradrenergic component of the contraction is modulated by the amount of noradrenaline released by sympathetic nerve firing, the density of post-junctional $\alpha_1$-adrenoceptors and their coupling to effector systems, and the rate at which noradrenaline is cleared from the synapse.

Antagonism at presynaptic $\alpha_2$-adrenoceptors is well recognised to enhance the electrically evoked release of noradrenaline from sympathetic nerves by blocking the activation of a negative feedback system by released noradrenaline. However, $\alpha_2$-adrenoceptor antagonism can not be the mechanism of action of $\chi$-MrIA. Unlike $\chi$-MrIA, $\alpha_2$-adrenoceptor antagonists such as yohimbine and idazoxan act to enhance equally the purinergic and noradrenergic components of the contraction of the rat vas deferens. Furthermore, the response to a single pulse, as opposed to a train of stimuli, is not subject to regulation by this negative feedback mechanism since there would be no agonist present at these receptor sites at the time of stimulation. Accordingly yohimbine (1 $\mu$M) has no effect on the evoked responses in this assay.

Example 2

Preparation to Examine Effect of $\chi$-MrIA on Responses to $\alpha_1$-adrenoceptor Agonists The rat vas deferens was used as described above, except that the bisected epididymal segments were not electrically stimulated. These preparations were instead used to establish concentration response curves to noradrenaline and methoxamine in the absence and presence of $\chi$-MrIA. In this tissue, noradrenaline and methoxaniine cause contraction of the smooth muscle via activation of postjunctional $\alpha_1$-adrenoceptors. $\chi$-MrIA at a concentration of either 1 $\mu$M or 3 $\mu$M was applied to the organ bath and allowed to equilibrate with the tissue for 20 min prior to cumulative additions of noradrenaline or methoxamine. A single concentration response curve was determined per preparation, with contralateral tissue segments to which $\chi$-MrIA was not applied serving as controls.

Effect of $\chi$-MrIA on Responses to $\alpha_1$-adrenoceptor Agonists

It was possible to determine whether the action of $\chi$-MrIA occurs upstream or downstream of neurotransmitter release by examining the effect of the peptide on the response to exogenously applied noradrenaline. Since $\chi$-MrIA enhanced the potency of bath-applied noradrenaline, we can conclude that the conotoxin acts by potentiating the response to noradrenaline, rather than by promoting its release from neuronal stores. This potentiation could occur as a consequence of increased $\alpha_1$-adrenoceptor responsiveness or impaired termination of the action of noradrenaline. The $\alpha_1$-adrenoceptor agonist methoxamine was used to ascertain which of these was the mechanism of action of $\chi$-MrIA. This $\alpha_1$-adrenoceptor agonist differs from noradrenaline in that it is not a substrate for the neuronal noradrenaline transporter. This transporter functions to eliminate noradrenaline and other catecholamines from the synapse by uptake into the nerve terminals, and represents the major mechanism for terminating the action of noradrenaline at the adrenoceptors of sympathetically innervated tissues. Because methoxamine is not subject to removal by this mechanism, inhibition of the transporter does not enhance the potency of its actions.

The effect of $\chi$-MrIA on the responses of the bisected segments of the rat epididymal vas deferens to two $\alpha_1$-adrenoceptor agonists was investigated. Log concentration-response curves to noradrenaline in the absence and presence of χ-MrIA are shown in FIG. 2a. At a concentration of 1 μM, χ-MrIA acted to increase the sensitivity of the tissue to noradrenaline, shifting the concentration response curve to the left. The degree of potentiation observed was larger in experiments with 3 μM χ-MrIA. Neither concentration of the conotoxin altered the maximum response of the tissue to noradrenaline. χ-MrIA at a concentration of 3 μM had no effect on the concentration response curve to methoxamine (FIG. 2b). The observation that χ-MrIA does not potentiate the action of methoxamine, in contrast to its effect on responsiveness to noradrenaline, is consistent with χ-MrIA being an inhibitor of the neuronal noradrenaline transporter.

The lack of effect of χ-MrIA on the concentration response curve to methoxamine also demonstrates that χ-MrIA has no effect at $\alpha_1$-adrenoceptors, which would be evident as a parallel shift of the curve to the right. This distinguishes χ-MrIA from some other inhibitors of noradrenaline transport, particularly those used as antidepressants. The therapeutic target of many of the antidepressant drugs is the neuronal noradrenaline transporter. However, many of these compounds, especially the tricyclic antidepressants, and to a lesser extent some newer drugs which are structurally unrelated to the conventional tricyclics, are recognised to act at other sites such as $\alpha_1$-adrenoceptors and muscarinic ACh receptors.

Example 3
Guinea-pig Ileum

Male guinea-pigs (285–425 g) starved overnight were killed by a blow to the head and exsanguinated. Segments of the ileum of approximately 1.5 cm length were removed and the luminal contents cleared by gentle washing using a syringe filled with bathing solution. The preparations were placed in 5 mL organ baths containing bathing solution of the following composition (mM): NaCl, 136.9; KCl, 2.68; $CaCl_2$, 1.84; $MgCl_2$, 1.03; glucose, 5.55; $NaHCO_3$, 11.9; and $KH_2PO_4$, 0.45; warmed to 37° C. and bubbled with 5% v/v $CO_2$ in $O_2$. Indomethacin (10 μM) was included in the bathing solution to produce a stable baseline. The tissues were placed under a tension of 1.0 g and allowed to equilibrate for 40 min prior to the commencement of experimentation. Doses of nicotine (4 μM) were then applied at 15 min intervals until the responses were observed to be consistent. χ-MrIA (3 μM) was then added, 25 min after which another dose of nicotine was applied. The responses to nicotine were measured isometrically and digitised at a sampling rate of 10 Hz.

Effect of χ-MrIA on Responses to Nicotine in the Guinea-pig Ileum

χ-MrIA (3 μM) had no significant effect on the responses of ileal segments to nicotine. In the absence of the conotoxin, the mean response was 3.83±0.76 g, compared to 4.07±0.80 g when χ-MrIA was present (p>0.1; paired t-test; n=4). The α-conotoxins block nicotinic ACh receptors of either the neuronal or muscle subtype. It was demonstrated that χ-MrIA does not target neuronal nicotinic ACh receptors using isolated segments of guinea-pig ileum. Because of the dependence of the contractile response on muscarinic receptor activation, it would be expected that the response of the guinea-pig ileum to nicotine would be attenuated in the presence of χ-MrIA if the conotoxin also acted as a muscarinic ACh receptor antagonist. In this preparation, the nicotine-induced release of ACh and various other neurotransmitters which activate postjunctional receptors was unaffected by χ-MrIA. Thus, and in contrast to many other transport inhibitors, χ-MrIA lacks anti-muscarinic activity.

Example 4
Mouse Phrenic Nerve-hemidiaphragm Preparation

Male Quackenbush mice (20–30 g) were killed by cervical dislocation. Left and right hemidiaphragms were removed with the phrenic nerves attached. The base of each hemidiaphragm was positioned between two parallel platinum stimulating electrodes and the phrenic nerve was placed through two small platinum loops for field stimulation. The preparation was incubated at 37° C. in a 5 mL organ bath bubbled with 5% v/v $CO_2$ in $O_2$. The composition of the bathing solution was (mM): NaCl, 135.0; KCl, 5.0; $CaCl_2$, 2.0; $MgCl_2$, 1.0; glucose, 11.0; $NaHCO_3$, 15.0; and $KH_2PO_4$, 1.0. The tissues were placed under 1.0 g resting tension. After allowing at least 30 min for equilibration, alternating direct and indirect stimulation was made at 10 s intervals using a 30 V pulse of 2 ms duration to the muscle, and a 3 V pulse of 0.2 ms duration to the nerve, respectively. The effect of a single dose of χ-MrIA at a concentration of 3 μM on the directly and indirectly elicited contractions was examined. Responses were digitised and recorded as described for the vas deferens preparations.

Effect of χ-MrIA on Responses to Electrical Simulation of the Mouse Phrenic Nerve-hemidiaphragm Contractions elicited by field stimulation of the phrenic nerve, or by direct muscle stimulation, were unaffected by 3 μM χ-MrIA (n=4). χ-MrIA does not block the muscle nicotinic ACh receptors in the mouse phrenic-nerve hemidiaphragm preparation. The lack of activity of χ-MrIA at skeletal muscle or motor nerve distinguishes it from the majority of conotoxin peptides characterised to date which are paralytic toxins and hence have a clear role in prey capture.

Example 5
Cellular Uptake of [$^3$H]-noradrenaline

Chinese hamster ovary (CHO) cells were grown in 24 well plates (Falcon) in 10% v/v fetal calf serum. On reaching 60–70% confluence, the cells were transiently transfected (Lipofectamine, Gibco) with an expression vector (pcDNA3, Invitrogen) incorporating the full length cDNA for the human neuronal noradrenaline transporter (Pacholczyk et al., (1991) Nature, 350, 350–4). A cDNA clone of the neuronal noradrenaline transporter was used (Vollum Institute, Portland, Oreg., USA). Cellular uptake studies were performed 36 hours after transfection. The CHO cells were initially washed with transport buffer containing (mM): NaCl, 157; KCl, 2.7; $NaH_2PO_4$, 11.8; $MgCl_2$, 1.0 and $CaCl_2$, 0.1; and of pH 7.4. The cells were then incubated with transport buffer containing 50 nM [$^3$H]-noradrenaline (supplemented with unlabelled noradrenaline as required) and 100 μM ascorbic acid. χ-MrIA (0.1 nM–1 μM) or desipramine (10 μM) were also included as appropriate. After 20 minutes at room temperature, the cells were rapidly washed with ice-cold phosphate buffered saline and then lysed in 0.1% v/v Triton-X. The cell lysates were taken for liquid scintillation counting to determine their level of radioactivity. Additionally, an aliquot of the cell lysate was used to measure protein concentration (BioRad DC protein assay). The specific uptake of [$^3$H]-noradrenaline by the noradrenaline transporter was defined as the component sensitive to desipramine (10 μM).

Effect of χ-MrIA on Cellular Accumulation of [$^3$H]-noradrenaline

The accumulation of noradrenaline into CHO cells expressing the human neuronal noradrenaline transporter was reduced to less than 0.5% of the control amount by desipramine (10 μM), demonstrating that the accumulation was due almost entirely to specific uptake via the cloned transporter. The noradrenaline transporter was confirmed as the target of the conotoxin in cellular uptake studies. χ-MrIA (0.1 nM–1 μM) inhibited the accumulation of radiolabelled noradrenaline in a concentration-dependent manner (FIG. 3), with a log $IC_{50}$ value of $-8.17\pm0.0275$ (n=4). The concentration of χ-MrIA required to inhibit the accumulation by 50% was found to be approximately 7 nM. This concentration is approximately one order of magnitude lower than that needed for desipramine to produce the same effect.

Cocaine and χ-MrIA are both naturally occurring compounds, however, they are quite dissimilar. Cocaine is an alkaloid extracted from the leaves of the coca plant, whereas χ-MrIA is a peptide directly encoded by an animal gene. In addition to its effect at the uptake transporter, cocaine is known to possess potent local anaesthetic properties. This is due to blockade of both sodium and potassium channels. No evidence was found for local anaesthetic activity of χ-MrIA in any of the assays. It was found that χ-MrIA had neither contractile nor relaxant effects on the tone of the vas deferens by itself. Similar studies revealed that χ-conotoxin does not inhibit the dopamine transporter.

Example 6

Tritiated mazindol binding to the noradrenaline transporter was measured in cells expressing the transporter protein (see Example 5). The influence of χ-MrIA from $10^{-6}$ to $10^{-9}$ on tritiated mazindol binding was measured. χ-MrIA had no effect on tritiated maizindol binding, indicating that it acts non-competitively, at a site distinct from traditional noradrenaline transport inhibitors, such as desipramine, mazindol and cocaine.

Example 7

Derivation of Gene Sequence for the χ-conotoxin Peptides

The complete gene sequence for the χ-MrIA was isolated using a combined 5' RACE (Random Amplification of cDNA Ends) and 3' RACE strategy coupled with cloning and DNA sequencing.

5'RACE

The oligonucleotide primer CHI-1B were designed from the mature peptide sequence. The relationship of the oligonucleotides to the peptide is as follows, together with the oligonucleotide sequence:

χ-MrIA-NGVCCGYKLCHPC SEQ ID NO. 3

CHI-1B 5'-CANGGRTGRCANARYTTRTA-3' SEQ ID NO. 4

AP1 5'-CCATCCTAATACGACTCACTATAGGGC-3' SEQ ID NO. 5

(where N=A/C/G/T, R=A/G, Y=C/T,)

Polymerase Chain Reaction (PCR) was carried out using the oligonucleotide CHI-1B in combination with the AP1 oligonucleotide on cDNA templates derived from the mRNA isolated from coneshell venom ducts. The PCR products, which represent the 5' region of the MrIA gene were isolated, purified, cloned into bacterial vectors and sequenced. Gene sequence for MrIA was obtained from *C. marmoreus* (FIG. 4).

3'RACE

The DNA sequence for the 5'-regions of the gene was used to design oligonucleotides that were capable of detecting the MrIA sequence, and sequences from other closely related peptides. The positioning of the oligonucleotides relative to the gene sequence is shown in FIG. 4. The oligonucleotide CH1-1A was used in PCR in conjunction with the ANCHOR oligonucleotide to produce DNA fragments corresponding to the leader peptide, mature peptide and 3' untranslated (3'UTR) regions of the gene. PCR of venom duct cDNA templates from *C. marmoreus* produced DNA fragments corresponding to the MrIA peptide.

The DNA sequences for the oligonucleotides are:

CHI-1A 5'-ACAGGCAGAATGCGCTGTCTCCC-3' SEQ ID NO. 6

ANCHOR 5'-AACTGGAAGAATTCGCGGCCGCAGGAAT-3' SEQ ID NO. 7

Complete Sequence for χ-MrIA

Gene sequence for χ-MrIA produced using 5' RACE and 3' RACE represent overlapping fragments of the gene. These fragments were combined, to produce a consensus sequence for the gene. The consensus sequence is the full cDNA for the gene, and includes 5' UTR, the leader peptide, the mature peptide and the 3' UTR. The χ-MrIA leader and mature peptide oligonucleotide sequence is shown in SEQ ID NO. 8, while the leader and mature peptide amino acid sequence is shown in SEQ ID NO. 9.

ATGCGCTGTCTCCCAGTCTTGATCAT-TCTTCTGCTGCTGACTGCATCTGCACCTGG CGTTGTTGTCCTACCGAAGACCGAAGAT-GATGTGCCCATGTCATCTGTCTACTGT AATG-GAAAGAGTATCCTACGAGGAATTCTGAG-GAACGGTGTGTGCTGTGGCTATA AGTTGTGCCATCCATGTTAA

SEQ ID NO. 8

MRCLPVLIILLLLTASAPGVVVLPKTED-DVPMSSVYCNGKSILRGILRNGVCCGYKLC HPC

SEQ ID NO. 9

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. An isolated, synthetic or recombinant χ-conotoxin peptide having the activity of inhibiting a neuronal amine transporter, wherein said χ-conotoxin peptide comprises MrIA as set forth in SEQ ID NO: 1 (NGVCCGYKLCHOC), or MrIB as set forth in SEQ ID NO: 2 (VGVCCGYKLCHOC), and wherein "O" represents 4-hydroxyproline.

2. An isolated, synthetic or recombinant χ-conotoxin peptide having the activity of inhibiting a neuronal amine transporter, wherein said χ-conotoxin peptide is MrIA as set forth in SEQ ID NO: 1 (NGVCCGYKLCHOC), and wherein "O" represents 4-hydroxyproline.

3. An isolated, synthetic or recombinant χ-conotoxin peptide having the activity of inhibiting a neuronal amine transporter, wherein said χ-conotoxin peptide is MrIB as set forth in SEQ ID NO: 2 (VGVCCGYKLCHOC), and wherein "O" represents 4-hydroxyproline.

4. A method for the treatment or control of pain in a mammal comprising administering to the mammal an amount of a χ-conotoxin peptide effective to control pain, wherein χ-conotoxin peptide comprises MrIA as set forth in SEQ ID NO: 1 (NGVCCGYKLCHOC), or MrIB as set forth in SEQ ID NO: 2 (VGVCCGYKLCHOC), and wherein "O" represents 4-hydroxyproline.

5. A method for the treatment or control of pain in a mammal comprising administering to the mammal an amount of a χ-conotoxin peptide effective to control pain, wherein χ-conotoxin peptide is selected from MrIA as set forth in SEQ ID NO: 1 (NGVCCGYKLCHOC), or MrIB as set forth in SEQ ID NO: 2 (VGVCCGYKLCHOC), and wherein "O" represents 4-hydroxyproline.

* * * * *

SEQUENCE LISTING

<160> NUMBER OF SEQ ID NOS: 9

<210> SEQ ID NO 1
<211> LENGTH: 13

-continued

```
<212> TYPE: PRT
<213> ORGANISM: Conus marmoreus
<220> FEATURE:
<221> NAME/KEY: PEPTIDE
<222> LOCATION: (12)
<223> OTHER INFORMATION: Xaa at position 12 is 4-hydroxy proline

<400> SEQUENCE: 1

Asn Gly Val Cys Cys Gly Tyr Lys Leu Cys His Xaa Cys
 1               5                   10

<210> SEQ ID NO 2
<211> LENGTH: 13
<212> TYPE: PRT
<213> ORGANISM: Conus marmoreus
<220> FEATURE:
<221> NAME/KEY: PEPTIDE
<222> LOCATION: (12)
<223> OTHER INFORMATION: Xaa at position 12 is 4-hydroxy proline

<400> SEQUENCE: 2

Val Gly Val Cys Cys Gly Tyr Lys Leu Cys His Xaa Cys
 1               5                   10

<210> SEQ ID NO 3
<211> LENGTH: 13
<212> TYPE: PRT
<213> ORGANISM: Conus marmoreus

<400> SEQUENCE: 3

Asn Gly Val Cys Cys Gly Tyr Lys Leu Cys His Pro Cys
 1               5                   10

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe
<220> FEATURE:
<221> NAME/KEY: unsure
<222> LOCATION: (3)
<223> OTHER INFORMATION: n=a/c/g/t
<220> FEATURE:
<221> NAME/KEY: unsure
<222> LOCATION: (6)
<223> OTHER INFORMATION: r=a/g
<220> FEATURE:
<221> NAME/KEY: unsure
<222> LOCATION: (9)
<223> OTHER INFORMATION: r=a/g
<220> FEATURE:
<221> NAME/KEY: unsure
<222> LOCATION: (12)
<223> OTHER INFORMATION: n=a/c/g/t
<220> FEATURE:
<221> NAME/KEY: unsure
<222> LOCATION: (14)
<223> OTHER INFORMATION: r=a/g
<220> FEATURE:
<221> NAME/KEY: unsure
<222> LOCATION: (15)
<223> OTHER INFORMATION: y=c/t
<220> FEATURE:
<221> NAME/KEY: unsure
<222> LOCATION: (18)
<223> OTHER INFORMATION: r=a/g

<400> SEQUENCE: 4
canggrtgrc anaryttrta                                              20
```

```
<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 5
ccatcctaat acgactcact atagggc                                          27

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 6
acaggcagaa tgcgctgtct ccc                                              23

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 7
aactggaaga attcgcggcc gcaggaat                                         28

<210> SEQ ID NO 8
<211> LENGTH: 186
<212> TYPE: DNA
<213> ORGANISM: Conus marmoreus

<400> SEQUENCE: 8
atgcgctgtc tcccagtctt gatcattctt ctgctgctga ctgcatctgc acctggcgtt      60
gttgtcctac cgaagaccga agatgatgtg cccatgtcat ctgtctactg taatggaaag     120
agtatcctac gaggaattct gaggaacggt gtgtgctgtg gctataagtt gtgccatcca     180
tgttaa                                                                186

<210> SEQ ID NO 9
<211> LENGTH: 61
<212> TYPE: PRT
<213> ORGANISM: Conus marmoreus

<400> SEQUENCE: 9

Met Arg Cys Leu Pro Val Leu Ile Ile Leu Leu Leu Leu Thr Ala Ser
 1               5                  10                  15

Ala Pro Gly Val Val Val Leu Pro Lys Thr Glu Asp Asp Val Pro Met
            20                  25                  30

Ser Ser Val Tyr Cys Asn Gly Lys Ser Ile Leu Arg Gly Ile Leu Arg
        35                  40                  45

Asn Gly Val Cys Cys Gly Tyr Lys Leu Cys His Pro Cys
    50                  55                  60
```